United States Patent [19]

Green

[11] Patent Number: 5,075,563
[45] Date of Patent: Dec. 24, 1991

[54] PHOTOMETER HEAD WITH HOUSING PORTIONS HAVING A GAP THEREBETWEEN

[75] Inventor: Andrew Green, Middlesex, United Kingdom

[73] Assignee: Eastman Kodak Company, Rochester, N.Y.

[21] Appl. No.: 424,280

[22] PCT Filed: May 26, 1988

[86] PCT No.: PCT/GB88/00413
§ 371 Date: Oct. 23, 1989
§ 102(e) Date: Oct. 23, 1989

[87] PCT Pub. No.: WO88/09528
PCT Pub. Date: Dec. 1, 1988

[30] Foreign Application Priority Data

May 29, 1987 [GB] United Kingdom ............... 8712633

[51] Int. Cl.⁵ .......................................... G01N 21/86
[52] U.S. Cl. .................................. 250/571; 250/239; 354/298
[58] Field of Search .............. 250/571, 239, 566; 354/298, 337; 356/443, 444; 235/435, 454, 462, 380, 381, 382

[56] References Cited

U.S. PATENT DOCUMENTS

| | | | |
|---|---|---|---|
| 3,677,150 | 7/1972 | Sanford | 356/443 |
| 4,260,880 | 4/1981 | Thomas | 250/566 |
| 4,293,226 | 10/1981 | Kinoshita et al. | 356/443 |
| 4,295,727 | 10/1981 | Robinson | 356/443 |
| 4,370,558 | 1/1983 | Kinoshita et al. | 356/443 |
| 4,396,902 | 8/1983 | Warthan et al. | 235/454 |
| 4,946,282 | 8/1990 | Task | 356/443 |
| 4,950,877 | 8/1990 | Kurihara et al. | 235/454 |
| 4,954,698 | 9/1990 | Yasunaga et al. | 235/454 |

FOREIGN PATENT DOCUMENTS 0041840 2/1989 Japan .

Primary Examiner—David C. Nelms
Assistant Examiner—S. Allen
Attorney, Agent, or Firm—G. Herman Childess

[57] ABSTRACT

A photometer head for measuring light transmission of a strip of photographic material has a base plate on which are mounted two housing portions. The housing portions have facing wall portions that are spaced apart to form a gap for receiving the strip, the base plate forming the bottom of the gap. The housing portions contain light source means for directing light to the gap and light sensitive means to receive light passing through the strip from the light source.

3 Claims, 1 Drawing Sheet

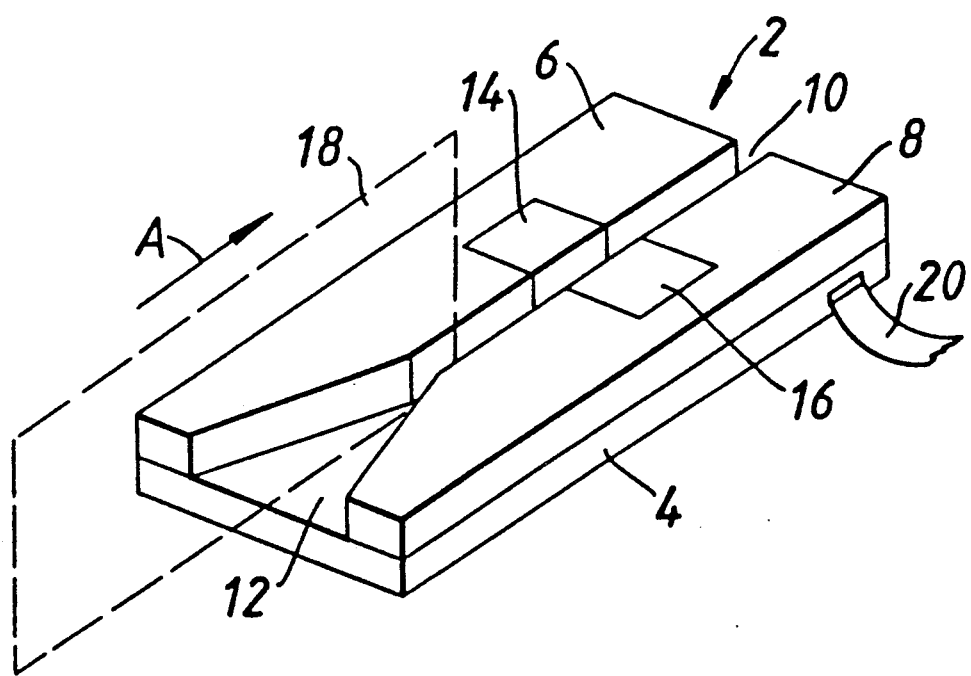

PHOTOMETER HEAD WITH HOUSING PORTIONS HAVING A GAP THEREBETWEEN

The present invention relates to densitometry. It relates in particular to measuring optical densities of, for example, photographic materials.

In photographic processing apparatus, such as used for X-ray materials, it is necessary to monitor the activity of processing solutions and if necessary replenish such solutions. A well-known technique for performing such a monitoring operation is to produce a process control strip of photographic material on which a series of graduated exposures have been produced, known as step wedges. The densities of such wedges are the measured in a densitometer so as to provide an indication of the state of the processing solutions in which the strip has been processed, and hence an indication of the need for replenishment.

U.S. Pat. No. 3,623,418 shows a densitometer having a measuring light source and photocell accommodated in different housing portions between which a strip is moved from a supply spool to a take-up spool.

The arrangement shown in U.S. Pat. No. 3,623,418 requires that the strip be of sufficient length to enable the use of the spools. If, however, the strip were very short, for example about 15 cm long, it would not be possible to use such an arrangement.

Other densiometers are shown in U.S. Pat. Nos. 4,057,818, 4,293,226; and 4,370,558.

In accordance with the present invention there is provided a densitometer head comprising a base plate on which are mounted two housing portions, a wall section of one housing portion being spaced from a wall section of the other housing portion so as to form a gap therebetween and the base plate forming a bottom of said gap, there being provided in one of said housing portions a light source and in said one or the other of said housing portions light-sensitive means which cooperates with the light source in the measurement of optical properties of strip of material passed through said gap, said gap being effective to locate said strip for such measurement, and resilient means in said gap for positioning such a strip of material whilst it passes therethrough.

THE DRAWINGS

The present invention will now be described, by way of example, with reference to the single FIGURE of the accompanying drawing which is a perspective view of a densitometer head of the present invention, with a strip of material to be measured being indicated by broken lines.

DETAILED DESCRIPTION OF THE INVENTION

The following description is directed in particular to photographic material. It is emphasised, however, that the apparatus and method are also applicable to other suitable materials.

A densitometer head 2 is provided with a base plate 4 on which are mounted housing portions 6 and 8. The housing portions 6 and 8 are spaced from each other to form a gap 10 which has a tapered entry portion 12 at one end of the head 2. In housing portion 6 is provided a light source, such as one or more LED's (light-emitting diodes) or one or more incandescent lamps, which is shown in a representative manner by the numeral 14.

In housing portion 8 is provided a light-sensitive device, such as one or more photodiodes, which is shown in a representative manner by the numeral 16. The light source 14 and light-sensitive device 16 are optically aligned with one another.

The light-sensitive device 16 is preferably resiliently urged by one or more springs (not shown) towards the light source 14. If desired, the light source 14 could be similarly resiliently urged. This has the effect of resiliently positioning a strip of material passing through the gap 10.

OPERATION

As an alternative to the light-sensitive device 16 and light source 14 being resiliently urged, they can be in fixed positions and plush provided along one or both opposing edges of the gap 10, so as to provide for resiliently positioning a strip of material passing through the gap 10.

In operation of the device a strip 18 of film to be measured is moved through the gap 10 in the direction of arrow A with its lower (as viewed in the FIGURE) longitudinal edge abutted against the upper (as viewed in the FIGURE) surface of the base plate 4. The tapered entry portion 12 provides a widened entryway to facilitate moving the strip 18 into the gap 10.

Movement of the strip 18 between the light source 14 and light-sensitive device 16 modifies the light received by the light-sensitive device 16 in accordance with the density of the strip 18. Signals representative of the density are produced and passed by means of connection 20 to a computer (not shown) for required manipulation.

Such manipulation of the signals by a computer may include producing a plot of density against time. In the case of a step wedge, this would be in a series of steps. Each step on the step wedge could have a marker, perhaps sensed by a further light-sensitive device, to indicate to the computer which part of the step wedge is being measured. The computer could convert the plot of density against time into a plot of density against log E (exposure).

Control parameters such as minimum density, maximum density, slope and speed could be calculated in the normal manner.

The device is particularly useful as a desk-top unit for measuring the film densities of step wedges provided on process control strips. As the step wedges are always arranged at the same distance from one of the longitudinal edges of the process control strips used, the densitometer head 2 is so arranged that during use the longitudinal edge of the sample adjacent to the step wedge contacts the upper surface of the base plate 4.

Compared to the arrangement in a conventional densitometer having a large table surface and a lowerable densitometer head, the arrangement provided by the densitometer head 2 offers the advantage that the individual step fields need not carefully be aligned with respect to the densitometer head 2 so as to avoid measuring errors; it will be sufficient to move the sample by hand in correct orientation (standing upright) through the densitometer head 2. If there is provided means for resiliently positioning the strip 18, a one-hand measuring operation is possible. It is emphasised, however, that the strip could be driven through the gap 10 by a motor-driven arrangement (not shown).

The apparatus described above could be used for black-and-white and/or colour measurements by utilising an appropriate light source, such as, for example, appropriately coloured LED's or incandescent lamps with one or more suitable filters.

As an alternative to the light source 14 and light-sensitive device 16 facing each other as described above, for measuring light transmittance, they could in fact be adjacent one another on the same side of the gap 10 for measurement of light reflection.

The densitometer described above can be utillised in a photographic processing apparatus for monitoring the state of the processing solutions and indicating whether their replenishment is necessary.

I claim:

1. A simple, low cost photometer head for measuring light transmission of a strip of photographic material moved through the head by hand and comprising:
    a flat base plate on which are mounted two upwardly extending housing portions having facing wall portions spaced apart to form a gap therebetween, open at the top and ends, for receiving the strip which is passed through the gap from one end of the gap to the other end strip, said base plate forming the bottom of said gap,
    said housing portions containing light source means for directing light to said gap and light sensitive means to receive light passing through said strip from said light source.

2. A photometer head as set forth in claim 1, further comprising:
    biasing means urging at least one of (a) said light source means and (b) said light sensitive means, toward said gap.

3. A photometer head as set forth in claim 1, further comprising:
    plush mounted on at least one side of said gap for resiliently positioning a strip of material passing therethrough.

* * * * *